(12) United States Patent
Friess et al.

(10) Patent No.: US 7,879,976 B2
(45) Date of Patent: Feb. 1, 2011

(54) METHOD FOR STABILIZING A PROTEIN

(75) Inventors: Wolfgang Friess, Iffeldorf (DE); Sylvia Kiese, Zurich (CH); Hanns-Christian Mahler, Basel (CH); Astrid Pappenberger, Bettingen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 476 days.

(21) Appl. No.: 12/109,435

(22) Filed: Apr. 25, 2008

(65) Prior Publication Data

US 2008/0275220 A1 Nov. 6, 2008

(30) Foreign Application Priority Data

May 2, 2007 (EP) .................................. 07107353

(51) Int. Cl.
*A61K 38/00* (2006.01)
*A61K 39/395* (2006.01)

(52) U.S. Cl. .................................................... 530/344

(58) Field of Classification Search ........................ None
See application file for complete search history.

(56) References Cited

U.S. PATENT DOCUMENTS

| 4,666,829 A | 5/1987 | Glenner et al. |
| 6,001,643 A * | 12/1999 | Spaulding ................ 435/298.2 |
| 2005/0260204 A1 | 11/2005 | Allan |
| 2007/0036779 A1 | 2/2007 | Bardat |
| 2007/0172475 A1 | 7/2007 | Matheus |

FOREIGN PATENT DOCUMENTS

| EP | 1541165 | 6/2005 |
| WO | WO 00/72880 | 12/2000 |
| WO | WO 03/070760 | 8/2003 |
| WO | WO 2004/103398 | 12/2004 |
| WO | WO 2005/005635 | 1/2005 |

OTHER PUBLICATIONS

Maa Y.F. et al, *Biotech and Bioeng.* 54:6 (1997) 503-512 XP002492210.
Frokjaer, S et al, *Nature Reviews, Drug Discovery*, (2005) 4:4 298-306 XP002492211.
Cleland et al *Critical Reviews in Therapeutic Drug Carrier Systems*, 10:4 (1993) 307-377 XP002083452.
Selkoe, (1994), Ann. Rev. Cell. Biol. vol. 10 pp. 373-403.
Koo, (1999) PNAS vol. 96 pp. 9989-9990.
Glenner (1984) BBRC vol. 122, pp. 1131-1135.
Sisodia (1992) PNAS vol. 89 pp. 6075-6079.
Sinha (1999) PNAS vol. 96, pp. 11049-11053.
Price (1998) Science vol. 282 pp. 1079-1083.
Hardy (1997) TINS vol. 20, pp. 154-159.
Jefferis (1998) Immunol. Rev. vol. 163 pp. 59-76.
Jefferis (2002) Immunol. Lett. vol. 82 (1-2) pp. 57-65.
Krapp (2003) J. Mol. Biol. vol. 325 (5) pp. 979-989.

* cited by examiner

*Primary Examiner*—Michael Pak
(74) *Attorney, Agent, or Firm*—George W. Johnston; Patricia S. Rocha-Tramaloni; Gene J. Yao (57) ABSTRACT

The invention relates to a method for stabilizing an aqueous protein solution against exogenous stress and to the use of a container for stabilizing an aqueous protein solution.

22 Claims, 9 Drawing Sheets

METHOD FOR STABILIZING A PROTEIN

PRIORITY TO RELATED APPLICATION(S)

This application claims the benefit of European Patent Application No. 07107353.0, filed May 2, 2007, which is hereby incorporated by reference in its entirety.

BACKGROUND OF THE INVENTION

The present invention relates to a method for stabilizing an aqueous protein solution against exogenous stress comprising the step of filing a container with said aqueous protein solution so that the container substantially lacks a gas headspace when closed.

Stabilization of aqueous protein solutions against exogenous stresses, e.g. mechanical stresses such as shaking, still represents a technical difficulty in the pharmaceutical industry. It is a known fact that aqueous protein solutions have a tendency to aggregate upon mechanical stress. Such mechanical stress almost always occurs upon transportation of the aqueous protein solution, e.g. in containers such as pharmaceutical vials.

A common solution adopted in the art is physico-chemical stabilization using, for instance, chemical stabilizers such as polysorbates such as Polysorbate 20 (also known as Tween 20™), Polysorbate 80 (Tween 80™), Poloxamer 188 and other surfactants.

However, it can be easily understood that stabilization without using chemical products would be of great advantage. In particular, the impact of chemical stabilizers on the safety of the human may be implicated. Therefore, regulatory authorities usually desire to minimize the number and quantity of chemical stabilizers included in a pharmaceutical formulation.

A lesser consideration compared to health concerns is the cost of chemical stabilizers that have to be added to stabilize an aqueous protein solution.

It hence clearly appears that there is a need for a method for stabilizing an aqueous protein solution against mechanical stress without using chemical stabilizers.

It is with this objective in mind that the Applicants found that an aqueous protein solution can surprisingly be stabilized against exogenous stress, e.g. mechanical stress, using a method comprising the step of filling a container with the aqueous protein solution so that the container substantially lacks a gas headspace when closed. Such a method does not require the use of chemical stabilizers.

This finding is even more surprising in view of the commonly established technical prejudice that has been overcome. Indeed, the method according to the invention overcomes the well known technical prejudice that chemical stabilizers must be used to stabilize an aqueous protein solution against mechanical stresses.

SUMMARY OF THE INVENTION

The present invention relates to a method for stabilizing an aqueous protein solution against exogenous stress comprising the step of filing a container with said aqueous protein solution so that the container substantially lacks a gas headspace when closed.

| Description of the Sequences | |
| --- | --- |
| SEQ ID NO: 1 | Amino acid sequence of the variable region of the Abeta antibody. |
| SEQ ID NO: 2 | Amino acid sequence of the light chain of the Abeta antibody. |
| SEQ ID NO: 3 | Amino acid sequence of Aβ42. |

DETAILED DESCRIPTION OF THE INVENTION

The present invention relates to a method for stabilizing an aqueous protein solution against exogenous stress comprising the step of filing a container with said aqueous protein solution so that the container substantially lacks a gas headspace when closed.

As used herein, the terms "stabilized" or "stabilizing" each mean that the aqueous protein solution substantially does not contain significant amounts of aggregation and/or turbidity and/or sub-visible particles and/or visible particles as measured with the corresponding tests described hereinafter in the examples.

As used herein, the expression "exogenous stress" refers to stress on the aqueous protein solution induced by an exogenous action. An "exogenous action" refers to an action coming from outside the system comprising the container and the aqueous protein solution. An example of exogenous stress is a mechanical stress. An example of mechanical stress is shaking. Shaking in the pharmaceutical industry can occur either accidentally, e.g. during transportation, or voluntarily, e.g. for homogenization of the solution.

As used herein, the term "container" refers to a pharmaceutically acceptable container. Suitable containers comprise a recipient part connected to an opening and a closing means. Preferably, the container consists of a recipient part connected to an opening and a closing means such as a regular pharmaceutically acceptable vial fitted with a closing cap, prefilled syringes, capsules or ampoules. Still more preferably, the container is a regular pharmaceutically acceptable vial fitted with a closing cap. The container can be fitted with hermetically closing means such as a cap hermetically closing the vial and protecting the aqueous protein solution from the surrounding outside atmosphere.

As used herein, the expression "aqueous protein solution" denotes an aqueous solution containing a protein. The protein concentration can range from 0.01 to 280 mg/mL.

As used herein, the expression "substantially lacks a gas headspace when closed" means that the person skilled in the art filling the container with the aqueous protein solution will fill the container up to the maximum volume of the container, said maximum volume being determined for examples visually or predetermined by calculation. This can be achieved, for example, by filling the container with the aqueous protein solution up to the maximum possible volume of the container, the precision of the measure being determined either visually in the laboratory by the meniscus formed by said solution at the maximum volume, gravimetrically by weighing the container, or volumetrically with standard equipments known in the art. The fill volume is meant to still allow adequate closure of the container without over-spilling.

As used herein, the expression "substantially lacks a gas headspace when closed" refers to the precision of a visual, gravimetric or volumetric determination of the maximum volume and/or lack of gas headspace, depending on the precision of the person handling the filling when determined visually or of the equipment used when the determination is gravimetric or volumetric.

As used herein, the term "usual pharmaceutically acceptable excipient" refers to an excipient contained already in marketed or other R&D products for administration to humans or animals. This term comprises: excipients from the class of buffers, including citrate, acetate, succinate, phosphate, histidine, glycine, and arginie buffers; amino acids, including arginine, glycine, lysine, tryptophane, and methionine; sugars or sugaralcohols, including sucrose, trehalose, mannitol, and sorbitol; surfactants, including polysorbate 20, polysorbate 80, poloxamer 188, sodiumdedecylsulfate, and triton X; and other excipients such as polyvinylpyrrolidone, cyclodextrines, polyethylenglycols; just to name a few.

As used herein, the terms "monoclonal antibody" and "monoclonal antibody composition" each refer to a preparation of antibody molecules of a single amino acid composition. Accordingly, the term "human monoclonal antibody" refers to antibodies displaying a single binding specificity which have variable and constant regions derived from human germline immunoglobulin sequences. In one embodiment, the human monoclonal antibodies are produced by a hybridoma which includes a B cell obtained from a transgenic non-human animal, e.g. a transgenic mouse, having a genome comprising a human heavy chain transgene and a light human chain transgene fused to an immortalized cell.

Antibody molecules, as part of the group of protein pharmaceuticals, are very susceptible to physical and chemical degradation, such as denaturation and aggregation, deamidation, oxidation and hydrolysis. Protein stability is influenced by the characteristics of the protein itself, e.g. the amino acid sequence, and by external influences, such as temperature, solvent pH, excipients, interfaces, shaking or shear rates. So, it is important to define the optimal formulation conditions to protect the protein against degradation reactions during manufacturing, storage and administration.

As used herein, the terms "anti-IGF-1R human monoclonal antibody" and "huMAb IGF-IR" each refer to an antibody as described and claimed in WO2005/005635, the content of which is incorporated herein by reference.

As used herein, "Abeta" refers to Abeta antibodies (or mixtures thereof) which are capable of specifically binding the amyloid-beta peptide. Antibodies that specifically bind Abeta are known in the art. Specific examples of Abeta antibody that can be used in the formulation according to the invention have been described in the published PCT patent application WO 03/070760, the content of which is incorporated herein by reference.

The amyloid-beta peptide, which is also termed "amyloid β", "Aβ", "Aβ4" or "β-A4" and, in particular in context of this invention, "Abeta", is a main component of the extracellular neuritic plaques that are associated with amyloidogenic diseases such as Alzheimer's disease; see Selkoe (1994), Ann. Rev. Cell Biol. 10, 373-403, Koo (1999), PNAS Vol. 96, pp. 9989-9990, U.S. Pat. No. 4,666,829 or Glenner (1984), BBRC 12, 1131. Amyloid β is derived from "Alzheimer precursor protein/β-amyloid precursor protein" (APP). APPs are integral membrane glycoproteins (see Sisodia (1992), PNAS Vol. 89, pp. 6075) and are endoproteolytically cleaved within the Abeta sequence by a plasma membrane protease, α-secretase (see Sisodia (1992), loc. cit.). Furthermore, further secretase activity, in particular β-secretase and γ-secretase activity, leads to the extracellular release of amyloid-β (Aβ) comprising either 39 amino acids (Aβ39), 40 amino acids (Aβ40), 42 amino acids (Aβ42) or 43 amino acids (Aβ43); see Sinha (1999), PNAS 96, 11094-1053; Price (1998), Science 282, 1078 to 1083; WO 00/72880 or Hardy (1997), TINS 20, 154.

Aβ has several naturally occurring forms, whereby the human forms are referred to as the above mentioned Aβ39, Aβ40, Aβ41, Aβ42 and Aβ43. The most prominent form, Aβ42, has the amino acid sequence (starting from the N-terminus): DAEFRHDSGYEVHHQKLVFFAEDVGSNKGAIIGLMVGGWIA (SEQ ID NO: 3).

In Aβ41, Aβ40, Aβ39, the C-terminal amino acids A, IA and VIA are missing, respectively. In the Aβ43-form an additional threonine residue is comprised at the C-terminus of the above depicted sequence (SEQ ID NO: 3).

Suitable Abeta antibodies are immunoglobulin molecules, e.g. IgG molecules. IgGs are characterized in comprising two heavy chains and two light chains (illustrated e.g. in FIG. 1) and these molecules comprise two antigen binding sites. Said antigen binding sites comprise "variable regions" consisting of parts of the heavy chains (VH) and parts of the light chains (VL). The antigen-binding sites are formed by the juxtaposition of the VH and VL domains. For general information on antibody molecules or immunoglobulin molecules see also common textbooks, like Abbas "Cellular and Molecular Immunology", W.B. Sounders Company (2003).

In one embodiment, the protein present in the aqueous protein solution of the present invention is an Abeta antibody (or mixture of such antibodies) in which in at least one of the variable regions in the heavy chain of said antibody comprises a N-glycosylation. The glycosylated asparagine (Asn) in the variable region of the heavy chain (VH) may be in the complementarity determining region 2 (CDR2), for example on position 52 in the variable region of the heavy chain (VH) as shown in SEQ ID NO: 1.

Figure 1:
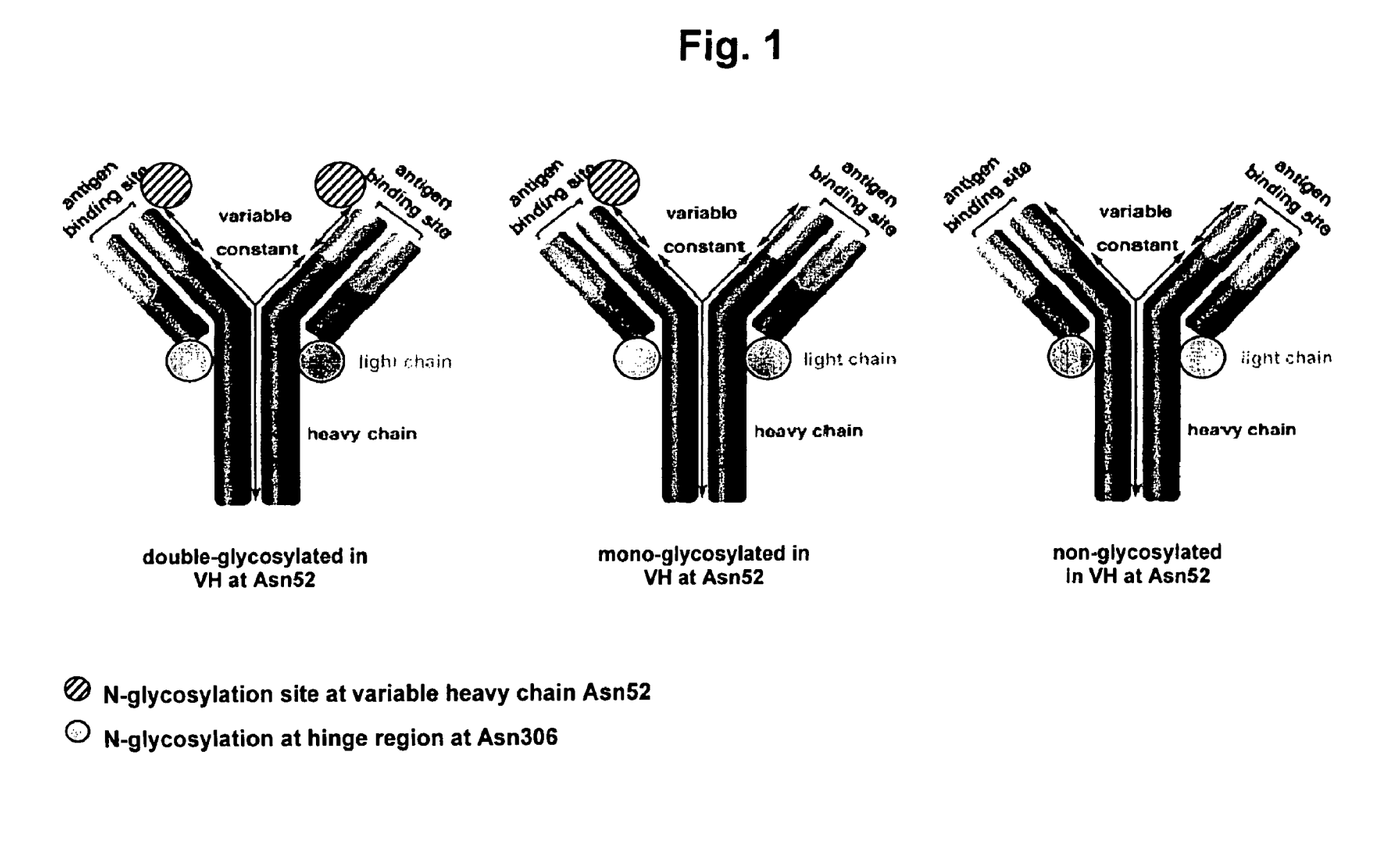
FIG. 1 shows the glycosylation sites of an Abeta antibody which can be stabilized in an aqueous solution according to the method of the invention.
Figure 2:
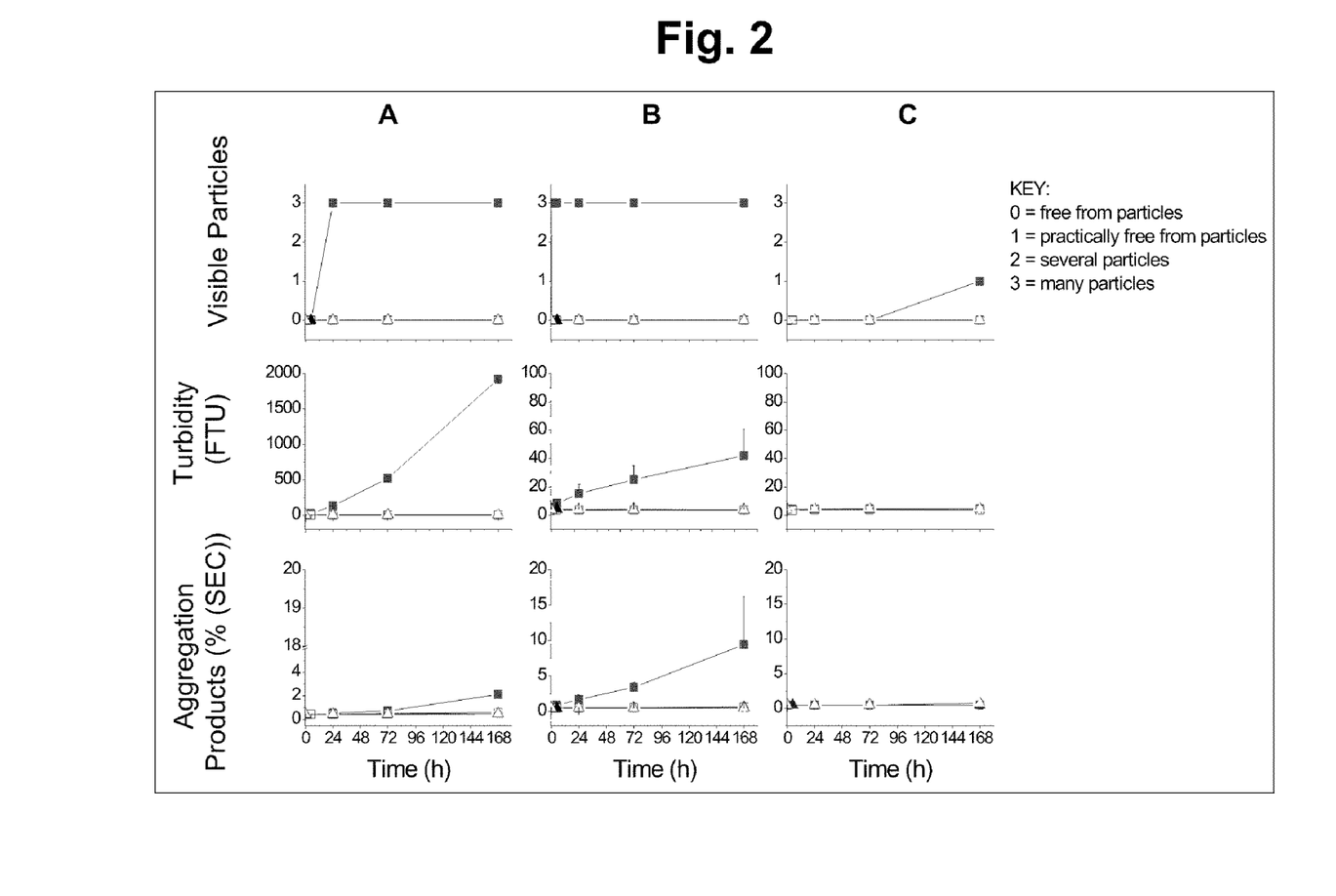
FIG. 2 shows the time course of 10 mg/ml antibody (Mab A) formulations under shaking stress at 5° C. at 3 fill volumes in 6 ml vials (A) 2.5 ml (B) 5.3 ml (C) 9.0 ml with various amounts of PS20 (■ 0%; □ 0.0025%; ▲ 0.005%; Δ 0.01%), analyzed by visual particle count, turbidity and soluble aggregate products.
Figure 3:
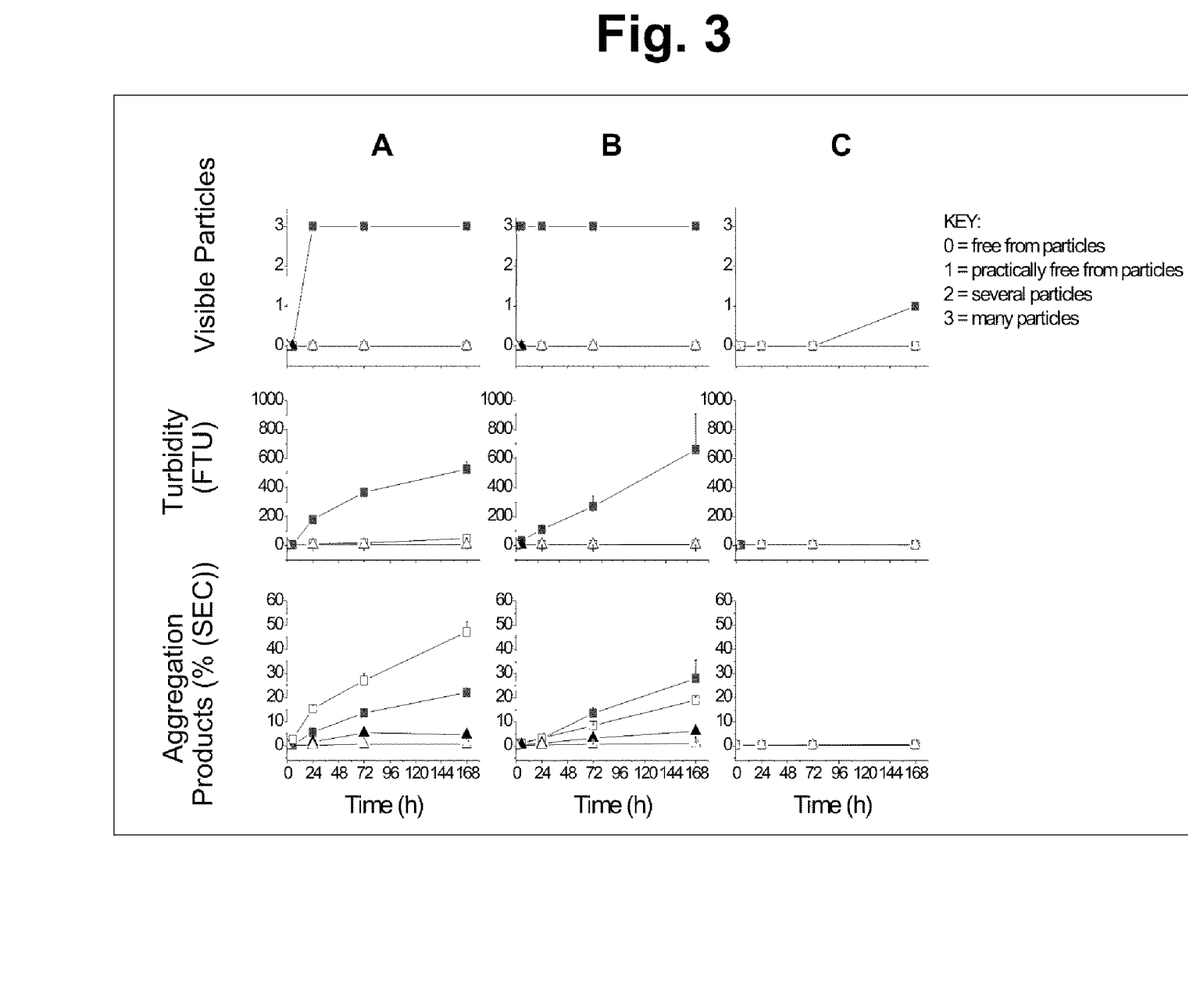
FIG. 3 shows the time course of 10 mg/ml antibody (Mab A) formulations under shaking stress at 25° C. at 3 fill volumes in 6 ml vials (A) 2.5 ml (B) 5.3 ml (C) 9.0 ml with various amounts of PS20 (■ 0%; □ 0.0025%; ▲ 0.005%; Δ 0.01%), analyzed by visual particle count, turbidity and soluble aggregate products.
Figure 4:
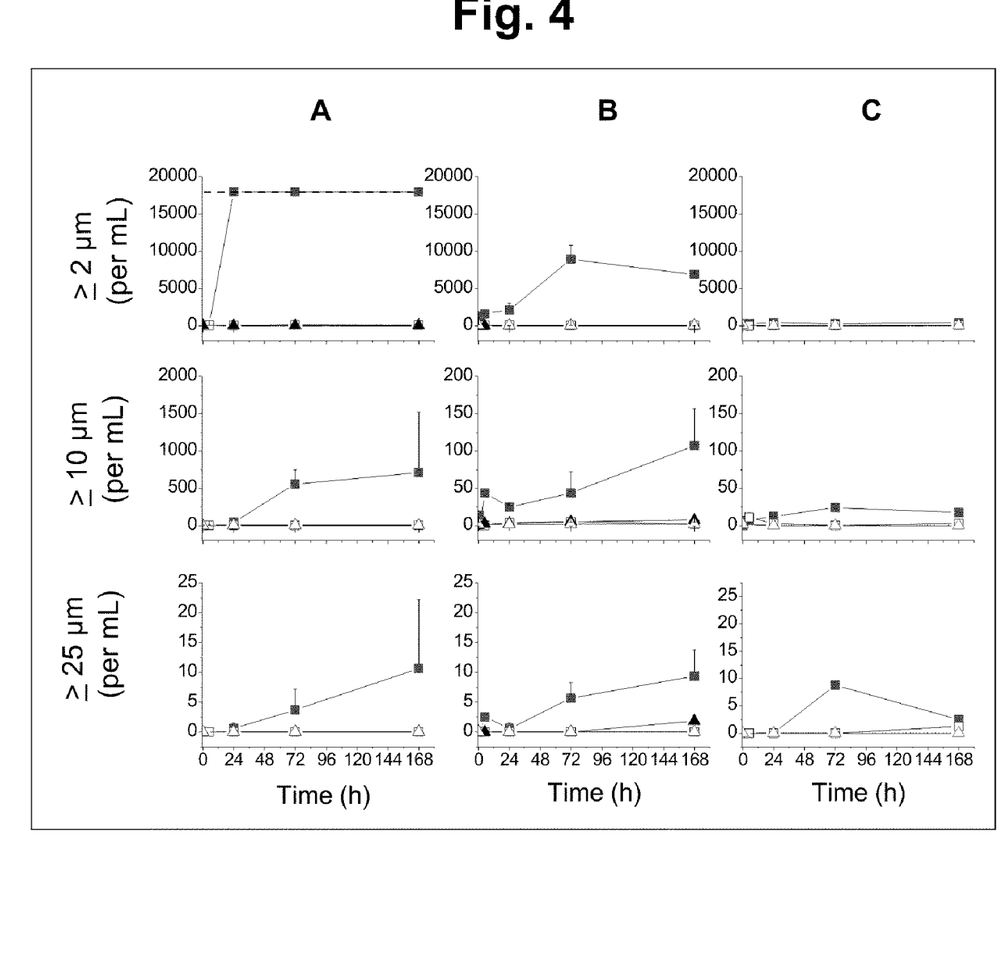
FIG. 4 shows the time course of 10 mg/ml antibody (Mab A) formulations under shaking stress at 5° C. at 3 fill volumes in 6 ml vials (A) 2.5 ml (B) 5.3 ml (C) 9.0 ml with various amounts of PS20 (■ 0%; □ 0.0025%; ▲ 0.005%; Δ 0.01%) analyzed by sub-visible particles at ≧2 μm, ≧10 μm and ≧25 μm per ml.
Figure 5:
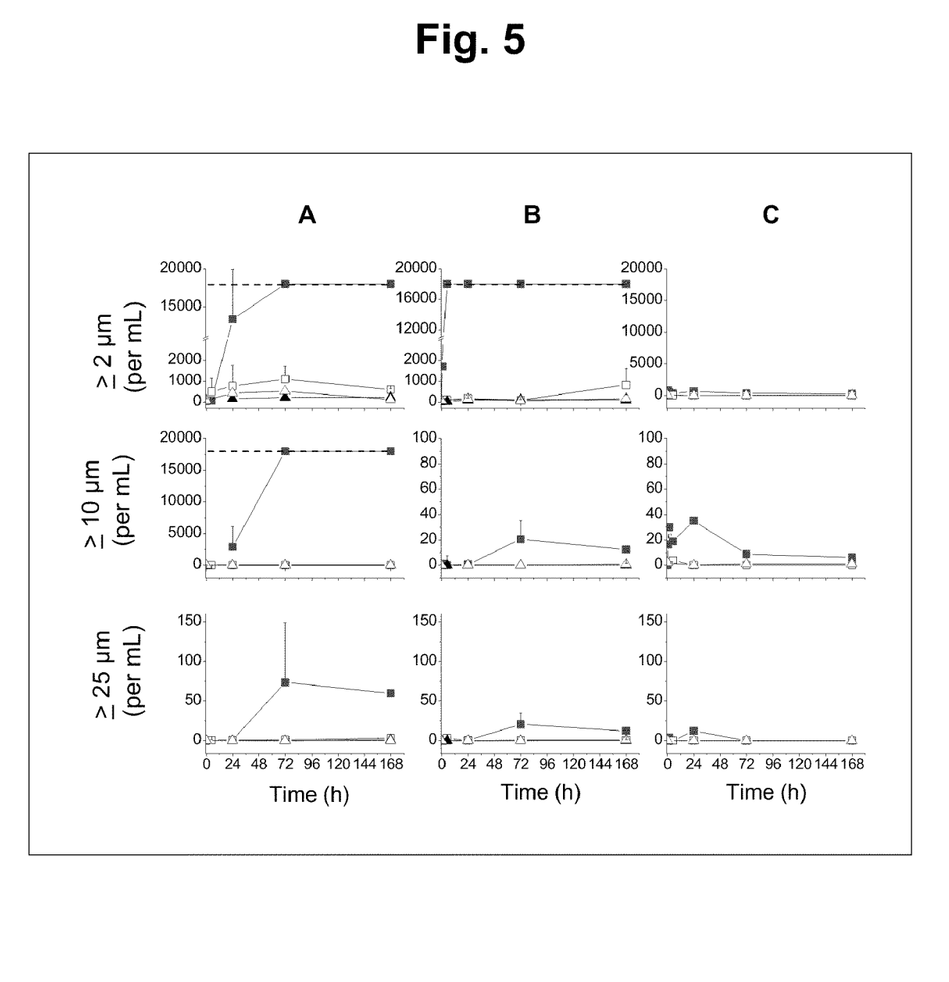
FIG. 5 shows the time course of a 10 mg/ml antibody (Mab A) formulation under shaking stress at 25° C. at 3 fill volumes in 6 ml vials (A) 2.5 ml (B) 5.3 ml (C) 9.0 ml with amounts of PS20 (0%; 0.0025%; 0.005%; Δ 0.01%) analyzed by sub-visible particles ≧2 μm, ≧10 μm and ≧25 μm per ml.

As used herein, the term "mono-glycosylated antibody" relates to an antibody molecule comprising an N-glycosylation in one ($V_H$)-region of an individual antibody molecule"; see also FIG. 1. As used herein, the term "double-glycosylation antibody" defines an antibody molecule which is N-glycosylated on both variable regions of the heavy chain" (FIG. 1). Antibody molecules which lack a N-glycosylation on both heavy chain ($V_H$)-domains are named herein "non-glycosylated antibodies" (FIG. 1). The mono-glycosylated antibody, the double-glycosylated antibody and the non-glycosylated antibody may comprise the identical amino acid sequences or different amino acid sequences.

The mono-glycosylated antibody and the double-glycosylated antibody are herein referred to as "glycosylated antibody isoforms" of each other. A purified antibody molecule characterized in that at least one antigen binding site comprises a glycosylation in the variable region of the heavy chain (VH) is a mono-glycosylated antibody which is free of or to a very low extent associated with an isoform selected from a double-glycosylated antibody and a non-glycosylated antibody, i.e. a "purified mono-glycosylated antibody". A double-glycosylated antibody in the context of this invention is free of or to a very low extent associated with an isoform selected from a mono-glycosylated antibody and a non-glycosylated antibody, i.e. a "purified double-glycosylated antibody".

The protein in the aqueous protein solution according to the method of the present invention may be mono-glycosylated, double-glycosylated or non-glycosylated antibodies, or specifically defined mixtures thereof. The antibody mixtures or antibody pools provided herein may comprise 50% mono-glycosylated and 50% double-glycosylated antibodies as defined herein. However, also envisaged are the ratios of: 30% mono-glycosylated and 70% double-glycosylated antibodies to 70% mono-glycosylated and 30% double-glycosylated antibodies. The person skilled in the art is aware that other ratios are also envisaged in the antibody mixtures of this invention. For example, ratios of mono-glycosylated to double-glycosylated antibodies may be 10:90, 90:10, 20:80, 80:20, 40:60, or 60:40. A particular useful ratio in the antibody mixtures comprised in the method of the invention comprises double-glycosylated and mono-glycosylated antibodies as defined herein above is a ratio from 40:60 to 45:55.

The term "which is free of or to a very low extent" denotes the complete absence of the respective other (glycosylation) isoforms or a presence of another (glycosylated) isoform in a concentration of at the most 10%, e.g. at the most 5%, e.g. at the most 4%, e.g. at the most 3%, e.g. at the most 2%, e.g. at the most 1%, e.g. at the most 0.5%, e.g. at the most 0.3%, e.g. at the most 0.2%.

The term "antibody(ies)" is used herein synonymously with the term "antibody molecule(s)" and comprises, in the context of the present invention, antibody molecule(s) like full immunoglobulin molecules, e.g. IgMs, IgDs, IgEs, IgAs or IgGs, like IgG1, IgG2, IgG2b, IgG3 or IgG4, as well as to parts of such immunoglobulin molecules, like Fab-fragments, Fab'-fragments, F(ab)2-fragments, chimeric F(ab)2 or chimeric Fab' fragments, chimeric Fab-fragments or isolated VH- or CDR-regions (said isolated VH- or CDR-regions being, e.g. to be integrated or engineered in corresponding "framework(s)") Accordingly, the term "antibody" also comprises known isoforms and modifications of immunoglobulins, like single-chain antibodies or single chain Fv fragments (scAB/scFv) or bispecific antibody constructs, said isoforms and modifications being characterized as comprising at least one glycosylated VH region as defined herein. A specific example of such an isoform or modification may be a sc (single chain) antibody in the format VH-VL or VL-VH, wherein said VH comprises the herein described glycosylation. Also bispecific scFvs are envisaged, e.g. in the format VH-VL-VH-VL, VL-VH-VH-VL, VH-VL-VL-VH. Also comprised in the term "antibody" are diabodies and molecules that comprise an antibody Fc domain as a vehicle attached to at least one antigen binding moiety/peptide, e.g. peptibodies as described in WO 00/24782. It is evident from the above that the aqueous protein solution used in the method of the present invention also comprises aqueous Abeta antibodies solutions including "mixtures" of antibodies/antibody molecules. A particular "mixture" of said antibodies is described above, namely a mixture of "mono" and "double"-glycosylated antibodies directed against Abeta.

"Antibody fragments" also comprises such fragments which per se are not able to provide effector functions (ADCC/CDC) but provide this function in a manner according to the invention after being combined with appropriate antibody constant domain(s).

The Abeta antibody(ies) that can be used as the protein in the aqueous protein solution in the method of the invention are, inter alia, recombinantly produced Abeta antibody(ies). These may be produced in a mammalian cell-culture system, e.g. in CHO cells. Such mammalian cell culture systems are particularly useful in the preparation of Abeta antibodies or Abeta antibodies/antibody molecules that are glycosylated like the specific herein exemplified Abeta antibody that comprises a N-glycosylation in the variable region. The antibody molecules may be further purified by a sequence of chromatographic and filtration steps e.g. in order to purify the specific glycosylated antibody isoforms as described herein below.

The terms "monoclonal antibody" or "monoclonal antibody composition" as used herein refer to a preparation of antibody molecules of a single amino acid composition. Accordingly, the term "human monoclonal antibody" refers to antibodies displaying a single binding specificity which have variable and constant regions derived from human germline immunoglobulin sequences. In one embodiment, the human monoclonal antibodies are produced by a hybridoma which includes a B cell obtained from a transgenic non-human animal, e.g. a transgenic mouse, having a genome comprising a human heavy chain transgene and a light human chain transgene fused to an immortalized cell.

The Abeta antibody can comprise or have the variable region as defined in SEQ ID NO: 1:

```
                                              (SEQ ID NO: 1)
QVELVESGGGLVQPGGSLRLSCAASGFTFSSYAMSWVRQAPGKGLEWVSA

INASGTRTYYADSVKGRFTISRDNSKNTLYLQMNSLRAEDTAVYYCARGK

GNTHKPYGYVRYFDVWGQGTLVTVSSASTKGPSVFPLAPSSKSTSGGTAA

LGCLVKDYFPEPVTVSWNSGALTSGVHTFPAVLQSSGLYSLSSVVTVPSS

SLGTQTYICNVNHKPSNTKVDKKVEPKSCDKTHTCPPCPAPELLGGPSVF

LFPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAKG
```

```
                            -continued
QPREPQVYTLPPSRDELTKNQVSLTCLVKGFYPSDIAVEWESNGQPENNY

KTTPPVLDSDGSFFLYSKLTVDKSRWQQGNVFSCSVMHEALHNHYTQKSL

SLSPGK
```

This sequence is also depicted herein below and the CDRs, CH-regions, heavy regions as well as two N-glycosylation sites (Asn 52 and Asn 306) are indicated:

(SEQ ID NO: 1)
```
QVELVESGGGLVQPGGSLRLSCAAS GFTFSSYAMS WVRQAPGKGLEWVS
AINASGTRTYYADSVKG RFTISRDNSKNTLYLQMNSLRAEDTAVYYCAR
GKGNTHKPYGYVRYFDV WGQGTLVTVSS ASTKGPSVFPLAPSSKSTSGGTAALGCL
VKDYFPEPVTVSWNSGALTSGVHTFPAVLQSSGLYSLSSVVTVPSSSLGTQTYICNVN
HKPSNTKVDKK VEPKSCDKTHTCP PCPAPELLGGPSVFLFPPKPKDTLMISRTPEVTC
VVVDVSHEDPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSLTCLVKGFYPSD
IAVEWESNGQPENNYKTTPPVLDSDGSFFLYSKLTVDKSRWQQGNVFSCSVMHEALH
NHYTQKSLSLSPGK
``` framed: CDR1, 2, 3 underlined: CH1 italics: hinge underlined twice: CH2 dotted underlined: CH3 bold N: N-linked glycosylation sites.

The exemplified Abeta antibody comprising SEQ ID NO: 1 as described herein may also comprise a light chain, said light chain may comprise or have the following amino acid sequence:

(SEQ ID NO: 2)
```
DIVLTQSPATLSLSPGERATLSCRASQSVSSSYLAWYQQKPGQAPRLLIY

GASSRATGVPARFSGSGSGTDFTLTISSLEPEDFATYYCLQIYNMPITFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC
```

The term "Abeta antibody A", as used herein, relates to the exemplified Abeta antibody comprising a heavy chain as defined in SEQ ID NO: 1 and a light chain as defined in SEQ ID NO: 2.

The term "mono-glycosylated antibody(ies)", as used herein, relates to antibody molecules comprising an N-glycosylation in one (VH)-region of an individual antibody molecule, for example, an immunoglobulin such as an IgG, e.g. IgG1. For example, said "mono-glycosylated form" comprises a glycosylation on one variable region of the heavy chain, for example at position asparagine "Asn 52" of the herein described "Abeta antibody A". This "mono-glycosylated IgG1-form or mono-glycosylated isoform" may also comprise, as illustrated herein, the glycosylation in the well conserved glycosylation site in the Fc-part, for example asparagine Asn 306 in the non-variable Fc-part of the herein exemplified "Abeta antibody A".

The term "double-glycosylated antibody(ies)" in the meaning of this invention comprises the herein defined glycosylation on both variable regions of the heavy chain (VH)-region. Again, this "double glycosylated form", comprises a glycosylation on the variable region of both heavy chains, for example at position asparagine Asn 52 of the herein exemplified "Abeta antibody A". This "double-glycosylated IgG1-form or double-glycosylated isoform" may also comprise, as illustrated herein, the glycosylation in the well conserved glycosylation site in the non-variable/constant Fc-part, in particular on position 306 of the exemplified "Abeta antibody A". Appended FIG. 1 illustrates corresponding antibody molecules.

Antibodies devoid of such a post-translational modification in the variable region, e.g. in both variable regions of the heavy chain (both (VH)-regions), are, in context of this invention, considered as "non-glycosylated form"s comprising no glycosylation in the variable region of the heavy chain. Yet, this "non-glycosylated form" may nevertheless comprise (a) glycosylation(s) in the constant region (C-region) of the antibody, most commonly at the well conserved glycosylation site of the Fc-part, in particular the asparagine (Asn) 306 in the non-variable/constant Fc-part as defined herein; see also SEQ ID NO: 1.

The protein in the aqueous protein solution in the method of the invention can be the exemplary "Abeta antibody A" as defined herein above. Accordingly, said protein can be Abeta antibody A comprising mono-glycosylated Abeta antibody A or double-glycosylated Abeta antibody A or non-glycosylated Abeta antibody A or mixtures thereof as defined above.

Purification of glycosylation isoforms of recombinantly expressed Abeta antibody molecules can comprise the steps of:

(1) protein A column purification;

(2) ion exchange column purification, e.g. a cation exchange chromatography; and, optionally, (3) size exclusion column purification.

The purification protocol may comprise further steps, like further concentration steps, e.g. diafiltration or analytical steps, e.g. involving analytical columns. It is also envisaged and feasible that particular certain steps are repeated (e.g. two ion exchange chromatography steps may be carried out) or that certain steps (e.g. size exclusion chromatography) may be omitted.

Protein A is a group specific ligand which binds to the Fc region of most IgG1 isotypes. It is synthesized by some strains of *Staphylococcus aureus* and can be isolated therefrom and coupled to chromatographic beads. Several types of gel preparations are available commercially. An example for a protein A column which may be used is a MabSelect (Trademark) column. Ideally the column is equilibrated with 25 mM Tris/HCl, 25 mM NaCl, 5 mM EDTA, the cell culture supernatant is loaded onto the column, the column is washed with 1 M Tris/HCl pH 7.2 and the antibody is eluted at pH 3.2 using 100 mM acetic acid.

Cation-exchange chromatography exploits interactions between positively charged groups in a stationary phase and the sample which is in the mobile phase. When a weak cation exchanger (e.g. CM Toyopearl 650®) is used, the following chromatographic steps are performed: After preequilibration with 100 mM acetic acid pH 4, loading of Protein A eluate and washing with 100 mM acetic acid pH 4, the antibody is eluted and fractionated by applying 250 mM sodium acetate (pH 7.8-8.5) and then 500 mM sodium acetate (pH 7.8-8.5). With the application of 250 mM sodium acetate, a mixture of double-glycosylated isoform fraction and mono-glycosylated isoform fraction is normally eluted. With the application of 500 mM sodium acdetate, the non-glycosylated isoform fraction is normally eluted.

From a strong cation exchanger (e.g. SP Toyopearl 650) the antibody can be eluted by salt steps: after equilibration of the column with 50 mM acetic acid pH 5.0 and loading the Protein A eluate with pH 4, the first elution step using 50 mM acetic acid and 210 mM sodium chloride is performed. Then a second elution step of 50 mM acetic acid and 350 mM sodium chloride is applied. In the first salt step, a mixture of the double-glycosylated isoform fraction and mono-glycosylated isoform fraction is normally eluted. With the second salt step the non-glycosylated isoform is normally eluted.

In addition the antibody may also be eluted from a strong cation exchanger column (e.g. SP-Sepharose®) by a salt gradient: After preequilibration, loading and washing the column at pH 4.5, a salt gradient is applied from 50 mM MES pH 5.8 to 50 mM MES/1 M sodium chloride pH 5.8. Here the double-glycosylated isoform, mono-glycosylated isoform and non-glycosylated isoform fractions are normally eluted separately. In the following double-glycosylated isoform fraction and mono-glycosylated isoform fraction may be pooled to result in the product pool and/or a desired antibody mixture.

Further purification of the mixture of double- and mono-glycosylated antibody molecules, e.g. immunoglobulins, may be performed by size exclusion chromatography. An example of a useful column is a Superdex 200®column. Examples of running buffers include histidine/sodium chloride, e.g. 10 mM histidine/125 mM sodium chloride/pH 6, and phosphate buffered saline (PBS).

Anion exchange chromatography in the flow through mode followed by a concentration/diafiltration is an alternative purification step. Q Sepharose® is an example of a resin for the anion exchange step. For example, the eluate from the SP chromatography may be threefold diluted with 37.5 mM Tris/HCl pH 7.9 and passed over a Q-Sepharose column pre-equilibrated with 25 mM Tris/83 mM sodium acetate. The flow through is collected, adjusted to pH 5.5 and concentrated by ultrafiltration using e.g. a Hydrosart 30 kD® membrane. In the following the concentrate may be diafiltrated against for example 10 volumes of 20 mM histidine/HCl pH 5.5.

As defined above, antibody isoforms may also comprise (a) further glycosylation(s) in the constant/non-variable part of the antibody molecules, e.g. in the Fc-part of an IgG, e.g. in the Fc-part in an IgG1. Said glycosylation in the Fc-part relates to a well conserved glycosylation, being characterized in located on position Asn306 of the heavy chain, e.g., in accordance with the herein defined SEQ ID NO: 1.

The IgG-Fc region of the antibodies comprised in the formulations of this invention may be a homodimer comprised of inter-chain disulphide bonded hinge regions, glycosylated CH2 domains, bearing N-linked oligosaccharide at aspar-agine 306 (Asn-306) of the CH2, and non-covalently paired CH3 domains. The oligosaccharide of the glycosylation at Asn-306 is of the complex biantennary type and may comprise a core heptasaccharide structure with variable addition of outer arm sugars.

The oligosaccharide influences or determines Fc structure and function (Jefferis (1998) Immunol Rev. 163, 50-76). Effector functions, numbering particular specific IgG-Fc/effector ligand interactions have been discussed (Jefferis (2002) Immunol Lett. 82(1-2), 57-65 and Krapp (2003) J Mol Biol. 325(5), 979-89). This conserved Fc-position Asn-306 corresponds to "Asn-297" in the Kabat-system (Kabat (1991) Sequences of Proteins of Immunological Interest, 5th Ed., Public Health Service, National Institutes of Health, Bethesda Md.)

The expression "stabilizer(s)" denotes pharmaceutically acceptable stabilizers able to chemically stabilize an aqueous protein solution against mechanical stresses. Examples of such stabilizers are surfactants, e.g. Tween 20, Tween 80, Tween 40, Tween 60, poloxamer, SDS or Triton X or any other amphiphilic molecule or mixtures thereof. The action of surfactants in aqueous solutions has been widely described in the art of which the person skilled in the art is well aware.

The expression "injection device" denotes a pharmaceutically acceptable injection device. An example of such device is a syringe.

As mentioned hereinabove, the present invention relates to a method for stabilizing an aqueous protein solution against exogenous stress comprising the step of filling a container with said aqueous protein solution so that the container substantially lacks a gas headspace when closed.

In any embodiment of the method according to the invention, the lack of gas headspace can be pre-determined, for example visually, gravimetrically or volumetrically.

In any embodiment of the method according to the invention the container can be filled at about more than 97% of the total volume of the container.

In any embodiment of the method according to the invention the gas headspace can represent less than about 3%, preferably 2% and still more preferably 1% of the total volume of the container In any embodiment of the method according to the invention the protein can be an antibody, in particular a monoclonal antibody, for example selected from the group consisting of IgG1 or IgG2 and IgG4 and preferably from the group consisting of monoclonal antibodies useful against at least one of the following targets: IGF-1R, CD20, CD19 CCR5, amyloid, OX40, EGF receptor, VEGF, HER, IL1R, IL13, IL6, IL17 and P-selecting.

The antibody can also be selected from the group consisting of those known and published in the art under the names Actemra, Avastin or Herceptin.

The method according to the invention can also be characterized by the fact that the aqueous protein solution lacks a stabilizer against exogenous stress, in particular mechanical stress.

In any embodiment of the method according to the invention, mechanical stress can be shaking. Mechanical stresses generally occur at a temperature of between about 0 to about 40° C.

The aqueous protein solution stabilized in the method according to the invention comprises water, a protein and other usual pharmaceutically acceptable excipients.

The method according to the invention can be characterized by the fact that, once stabilized, the aqueous protein solution substantially lacks significant turbidity and/or aggregation and/or visible particles upon shaking.

In a certain embodiment of the method according to the invention, the container is not an injection device, for example it is not a syringe.

The container can comprise a recipient part connected to an opening and a closing means. In a certain embodiment, the container consists of a recipient part connected to an opening and a closing means, preferably a recipient part connected to an opening and a hermetically closing means.

The invention also relates to the use of a container comprising a recipient part connected to an opening and a closing means for stabilizing an aqueous protein solution against mechanical stress. Said use can be made according to the method of the invention as described hereinabove.

The following examples are meant to illustrate the invention without limiting it to the sole embodiments disclosed therein.

EXAMPLES

In the following examples, the aggregation behavior of two monoclonal antibodies (IgG1) was investigated under shaking stress, at two different temperatures, various fill volumes and different amounts of polysorbate. The detection and monitoring of aggregate formation in terms of size and number was carried out with the use of various analytical techniques: visual inspection, turbidity, light obscuration, size-exclusion chromatography and dynamic light scattering.

The dimensions of the 6 ml Ø 20 mm glass vial were used to determine the container volume and the surface area which in turn was used to calculate the degree of the air-liquid interfaces for each fill volume by the ratios surface area to volume and headspace to volume. All experiments presented in the examples were carried in such vials.

From the tables 1 and 2 hereinafter, the lower the fill volume the higher the headspace volume which is an important aspect during shaking experiments for amount of gas volume to interact with the liquid sample. Samples filled to the maximum volume lack a headspace and physical movement of the liquid within the vial during shaking is limited. The ratio of surface area to fill volume increases with the decrease of fill volume, which allows more contact of the glass surfaces during agitation (table 2).

TABLE 1

The calculated surface area and container volume of a 6 ml Ø20 mm vial

| | Surface Area | | Container Volume |
|---|---|---|---|
| Bottom area | 314.2 mm$^2$ | — | — |
| Container body | 1401.2 mm$^2$ | Container body | 7005.8 mm$^3$ |
| Truncated con | 460.9 mm$^2$ | Truncated con | 955.2 mm$^3$ |
| Container neck | 336.5 mm$^2$ | Container neck | 1059.9 mm$^3$ |
| Total area | 25 cm$^2$ | Total area | 9.0 ml |

TABLE 2

The calculated ratios of surface area to fill volume and headspace to fill volume

| Test | 2.5 ml/6 ml "Empty" | 5.3 ml/6 ml "Nominal" | 9 ml/6 ml "Full" |
|---|---|---|---|
| Vial size | 6 ml Ø20 mm | 6 ml Ø20 mm | 6 ml Ø20 mm |
| Fill volume | 2.5 ml | 5.3 ml | 9.0 ml |
| Headspace:fill volume ratio | 2.61 cm$^3$/cm$^3$ | 0.70 cm$^3$/cm$^3$ | 0.00 cm$^3$/cm$^3$ |
| Surface area:fill volume ratio | 10.05 cm$^2$/cm$^3$ | 4.74 cm$^2$/cm$^3$ | 2.79 cm$^2$/cm$^3$ |

The shaking study at various fill volumes (2.5 ml, 5.3 ml and 9 ml) in a 6 ml nominal volume vial, closed with a rubber stopper and aluminum seal, was performed by observing the time course of protein formulations with PS20 at 0%, 0.0025%, 0.005% and 0.01% (w/v) at selected time points over a period of 168 hours at 5° C. and 25° C. This was carried out in order to evaluate the influence of a headspace on the stability of a protein during shaking since the air-liquid or liquid-glass interfaces to which the protein is exposed to is based on the volume of air-liquid present in the sample vial. The degree to which the PS20 protected the protein from these interfaces and thus against denaturation and aggregation during shaking was also assessed. The results of turbidity, visual particle count, sub-visible particles and soluble aggregate products as a result of shaking stress are summarized in FIGS. 2-9.

From the above results (FIG. 2-9), the presence of a headspace in the vials had a great influence on the stability of the antibody formulation when stressed by shaking at both temperatures of 5° C. and 25° C.

All formulations at "maximum" fill volume (FIGS. 2-5, columns C and FIGS. 6-7, columns D) as well as the placebos as controls (data not shown) remained stable where the stressed samples exhibited comparable results to the unstressed samples.

Samples filled to the maximum volume lack a significant headspace (less then 3% headspace volume) and therefore movement of the liquid within the vial is suppressed and no damage to the protein is seen.

With a "standard" headspace as used in regular pharmaceutical drug products in the market, the liquid sample has the ability to whirl and splash within the vial during shaking which results in the air-liquid interaction leading to protein instability.

The liquid of all samples moved in the same manner as each formulations had a dynamic viscosity of 1.1158±0.002 mPa·s. A difference on the protein stability between shaking with and without a headspace was evident whilst no significant variations were seen between samples shaken with headspace at a volume of 2.5 ml or 5.3 ml.

Figure 6:
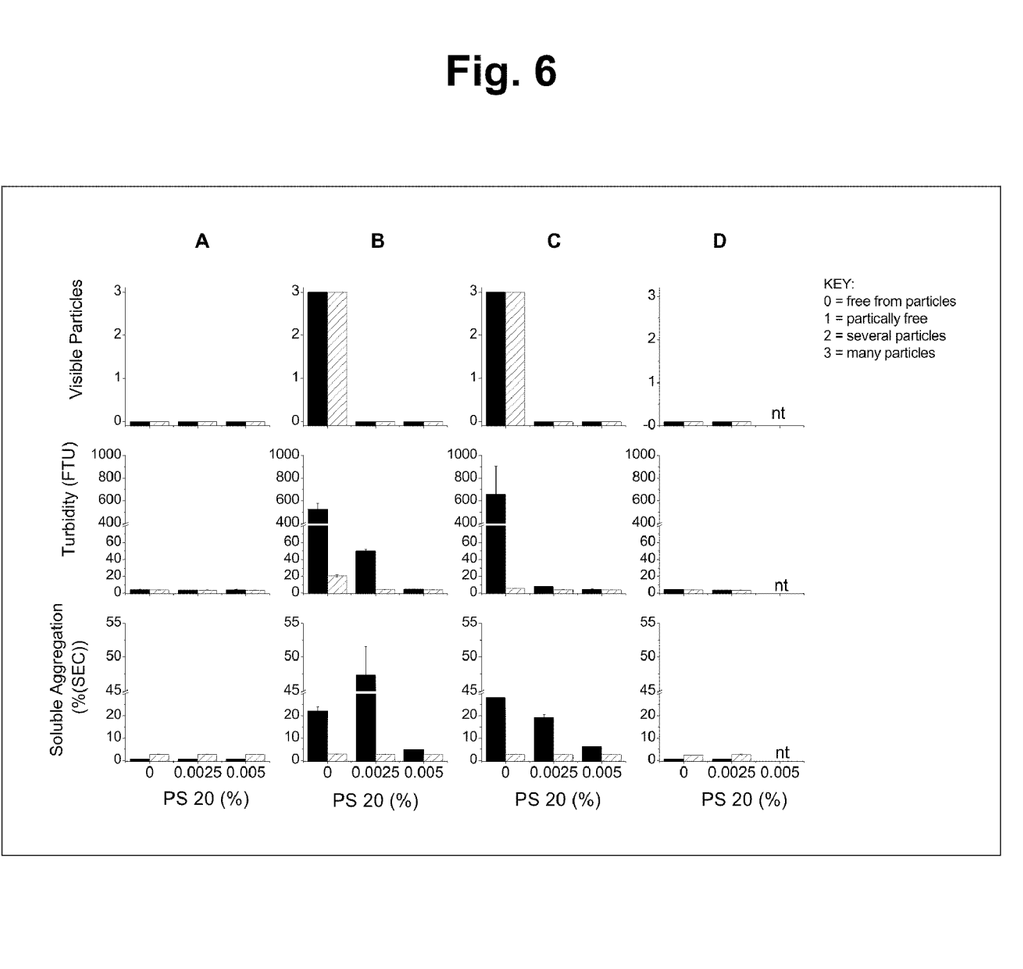
FIG. 6 shows the aggregation formation of two 10 mg/ml antibodies Mab A and Mab B under (A) unstressed conditions and 72 hours shaking stress at 25° C. at 3 fill volumes in 6 ml vials (B) 2.5 ml (C) 5.3 ml (D) 9.0 ml with various amounts of PS20 (0%; 0.0025%; 0.005%), analyzed by visual particle count, turbidity and soluble aggregate products.
Figure 7:
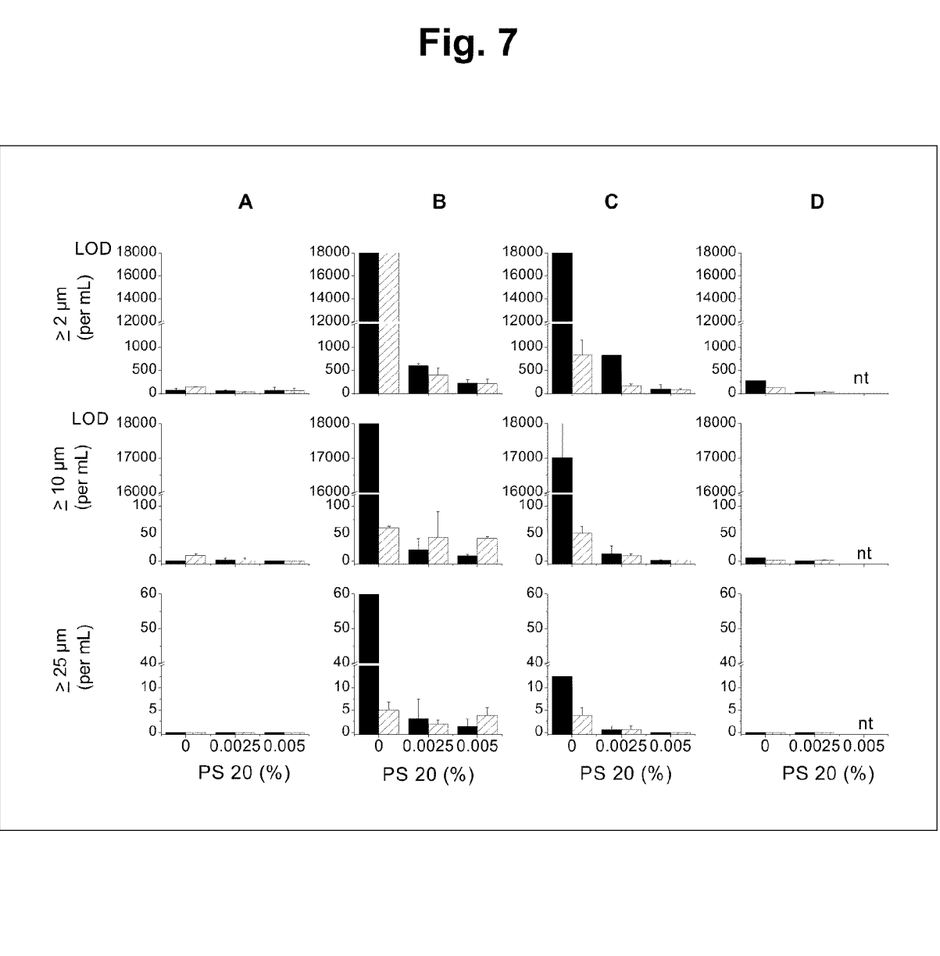
FIG. 7 shows the aggregation formation of two 10 mg/ml antibodies Mab A and Mab B under (A) unstressed conditions and 72 hours shaking stress at 25° C. at 3 fill volumes in 6 ml vials (B) 2.5 ml (C) 5.3 ml (D) 9.0 ml with various amounts of PS20 (0%; 0.0025%; 0.005%), analyzed by sub-visible particles at ≧2 μm, ≧10 μm and ≧25 μm per ml.
Figure 8:
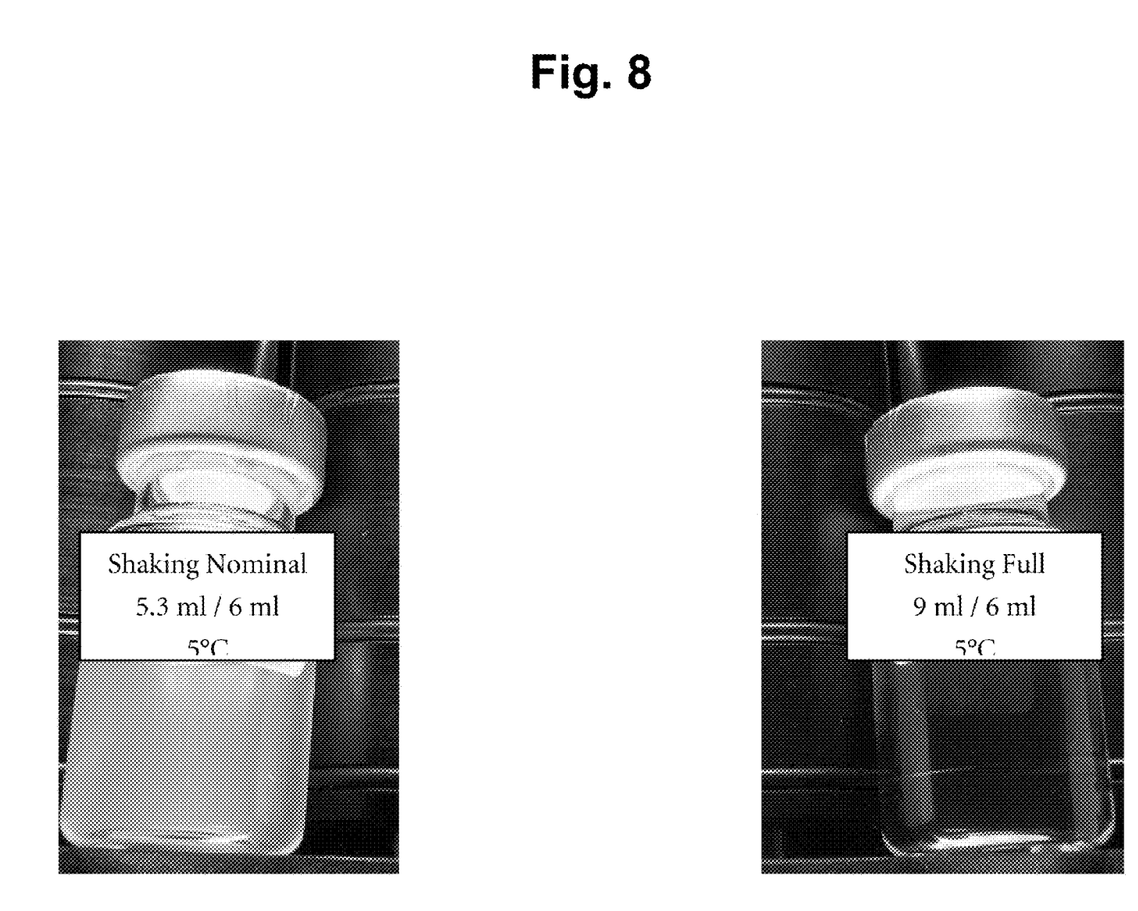
FIGS. 8 and 9 show pictures of containers (here pharmaceutically acceptable vials) filled with an aqueous protein solution after exogenous stress (here mechanical stress). On the left hand side are shown containers containing a protein solution with a gas headspace when closed like it is the case in the prior art. On the right hand side are shown containers containing a protein solution substantially lacking a gas headspace when closed according to the method of the invention.
Figure 9:
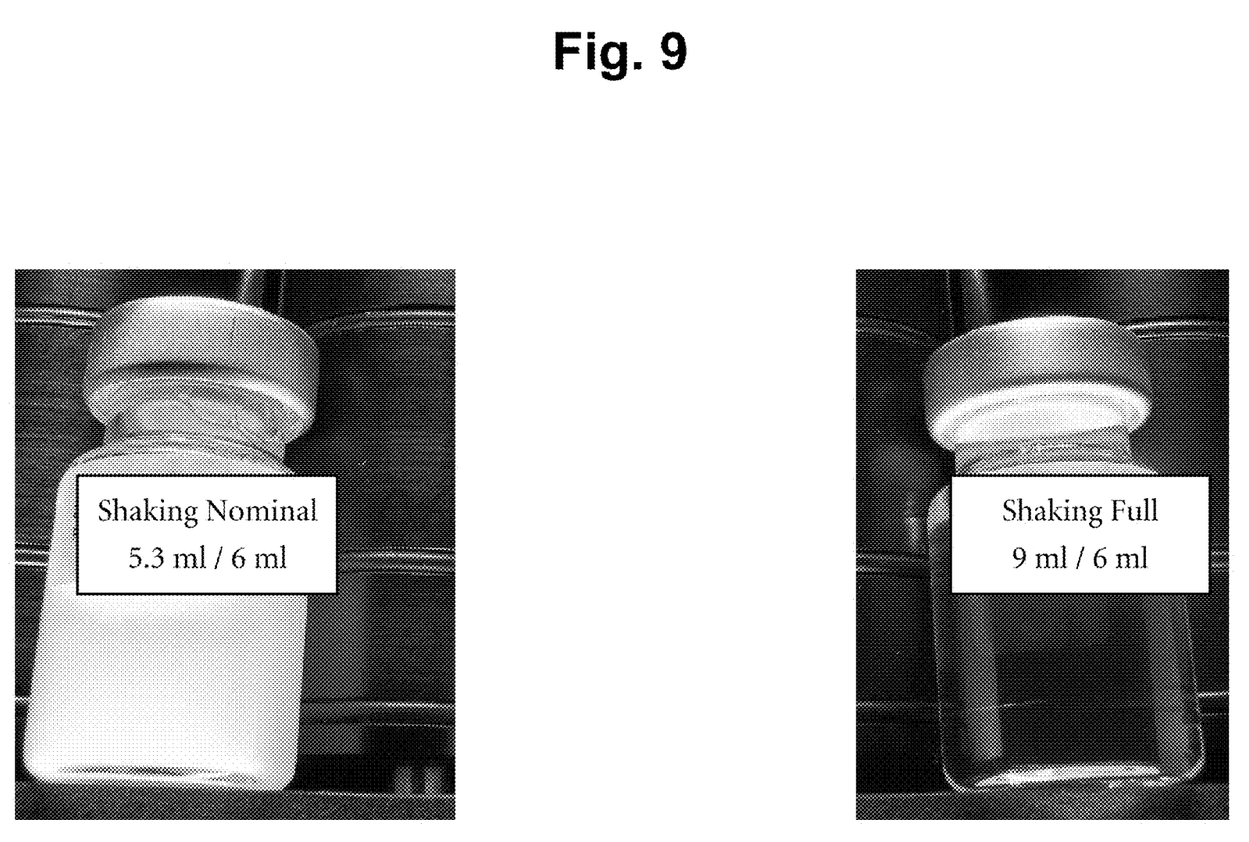

The presence of as little as 0.0025% PS20 gave similar protection to the proteins in the empty and nominal filling (FIGS. 2-5, columns A and B; FIGS. 6-7, columns B and C) as samples without PS and filled to the maximum (FIGS. 2-5, columns C; FIGS. 6-7, column D) when analyzed in terms of visible particle count, turbidity and sub-visible particle count at both temperatures.

However, whereas 0.0025% PS20 was sufficient to prevent soluble aggregate formation for Mab A at 5° C. (FIG. 2, bottom row) significantly higher amounts (0.01% PS20) were needed under the 25° C. shaking conditions (FIG. 3, bottom row) for the inhibition of aggregation products as analyzed by SEC.

Thus, the negative effect of shaking stress on soluble aggregate formation is far more evident at 25° C. compared to 5° C. especially for samples with a headspace (2.5 ml and 5.3 ml).

However, at 5° C. the turbidity of the sample with a 2.5 ml fill volume at 0% PS20 resulted in much higher FTU values throughout the study than at 25° C. This turbidity result does not correspond to the data obtained by sub-visible particle count and soluble aggregate analysis for the same sample of Mab A.

Turbidity is described as the cloudiness or haziness of a solution caused by sub-visible individual particles of various sizes, which scatter and absorb light giving the optical property of the liquid.

The samples of Mab A and B with nominal fill volume of 5.3 ml (FIGS. 3, B, 6, C and 7,C) showed the expected trend of a decrease of soluble aggregates and sub-visible particles with the increase of PS20 content. A strong dependency of soluble aggregate formation with PS20 concentration was also seen in the fill volume of 2.5 ml of Mab A (FIG. 3, A, bottom row), but in contrast to the sample with a fill volume of 5.3 ml, the 0.0025% PS20 formulations resulted interestingly in higher amounts of aggregates then at 0% PS20.

Overall, the data show that during formulation development, the shaking sample filled to the "maximum" (i.e. with minimal headspace) showed that no PS is required to inhibit particle or aggregation formation (FIGS. 2-5, columns C, FIGS. 6-7, columns D) whereas if a sample with a regular headspace is stressed, PS would be needed as a stabilizer. All commercially available liquid protein formulations within glass vials contain a headspace (with the exception of pre-filled syringes). There are at present no guidelines or specifications to the obligatory headspace volume required for vials containing protein solutions. For a commercial product filling without headspace or with a minimal headspace (as defined as 97% fill volume of closure) would be of great benefit to the stability of a biopharmaceutical product and would allow minimizing stabilizers needed in the protein solution. The absence of PS20 results in a great number of sub-visible particles yet this is completely inhibited in the absence of a headspace of the same formulation.

A further point is the importance of orthogonal methods when analyzing aggregates. As in this case, basing stability of a formulation on turbidity analyses alone would gave an indication that 0.0025% P20 was sufficient to protect the protein during shaking at 25° C. whereas in contrast more than 0.005% PS20 is necessary when considering the SEC data.

The data showed the presence of a headspace in the vials had a great influence on the stability of the protein formulation when stressed by shaking.

Samples filled to the maximum volume lack a significant headspace and therefore movement of the liquid within the vial was suppressed and no damage to the protein was seen during shaking.

The elimination of a headspace had similar protective properties on a formulation in the absence of PS20 as a formulation with 0.0025% PS20 when shaken with a headspace to volume ratio of 0.70 $cm^3/cm^3$ and 2.61 $cm^3/cm^3$, where no significant difference was seen between the two volumes.

The invention claimed is:

1. A method for stabilizing an aqueous protein solution against exogenous stress comprising the step of filling a container with said aqueous protein solution so that the container substantially lacks a gas headspace when closed.

2. The method according to claim 1, wherein the lack of gas headspace is pre-determined either visually, gravimetrically or volumetrically.

3. The method according to claim 1 wherein the container is filled at about more than 97% of the total volume of the container.

4. The method according to claim 1 wherein the gas headspace represents less than about 3% of the total volume of the container.

5. The method according to claim 1 wherein the gas headspace represents less than about 2% of the total volume of the container.

6. The method according to claim 1 wherein the gas headspace represents less than about 1% of the total volume of the container.

7. The method according to claim 1, wherein the protein is an antibody.

8. The method according to claim 1, wherein the protein is a monoclonal antibody.

9. The method according to claim 8, wherein the monoclonal antibody is selected from the group consisting of: IgG1, IgG2, and IgG4.

10. The method according to claim 9, wherein the monoclonal antibody is against at least one of the following targets: IGF-1R, CD20, CD19 CCR5, amyloid, OX40, EGF receptor, VEGF, HER, IL1R, IL13, IL6, IL17 and P-selecting.

11. The method according to claim 10, wherein the monoclonal antibody is selected from the group consisting of: Actemra, Avastin, and Herceptin.

12. The method according to claim 1 wherein the aqueous protein solution lacks a stabilizer against exogenous stress.

13. The method according to claim 12 wherein the exogenous stress is a mechanical stress.

14. The method according to claim 13 wherein the mechanical stress is shaking.

15. The method according to claim 1 wherein the exogenous stress occurs at a temperature of between 0 to 40° C.

16. The method according to claim 1 wherein the aqueous protein solution comprises water and a protein.

17. The method according to claim 1 wherein the aqueous protein solution comprises pharmaceutically acceptable excipients.

18. The method according to claim 1 wherein the aqueous protein solution substantially lacks significant turbidity and/or aggregation and/or visible particles upon shaking.

19. The method according to claim 1 wherein the container is not an injection device.

20. The method according to claim 1 wherein the container is not a syringe.

21. The method according to claim 1 wherein the container comprises a recipient part connected to an opening and a closing means.

22. The method according to claim 1 wherein the container consists of a recipient connected to an opening and a closing means.

* * * * *

SEQUENCE LISTING

```
<160> NUMBER OF SEQ ID NOS: 3

<210> SEQ ID NO 1
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Glu Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ala Ser Gly Thr Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Lys Gly Asn Thr His Lys Pro Tyr Gly Tyr Val Arg Tyr
            100                 105                 110

Phe Asp Val Trp Gly Gln Gly Thr Leu Val Thr Val Ser Ser Ala Ser
        115                 120                 125
```

```
Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
        195                 200                 205

Cys Asn Val Asn His Lys Pro Ser Asn Thr Lys Val Asp Lys Lys Val
210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 2
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30
```

```
Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Val Pro Ala Arg Phe Ser
        50                  55                  60

Gly Ser Gly Ser Gly Thr Asp Phe Thr Leu Thr Ile Ser Ser Leu Glu
 65                  70                  75                  80

Pro Glu Asp Phe Ala Thr Tyr Tyr Cys Leu Gln Ile Tyr Asn Met Pro
                 85                  90                  95

Ile Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
    210                 215

<210> SEQ ID NO 3
<211> LENGTH: 42
<212> TYPE: PRT
<213> ORGANISM: Homo sapiens

<400> SEQUENCE: 3

Asp Ala Glu Phe Arg His Asp Ser Gly Tyr Glu Val His His Gln Lys
 1               5                  10                  15

Leu Val Phe Phe Ala Glu Asp Val Gly Ser Asn Lys Gly Ala Ile Ile
            20                  25                  30

Gly Leu Met Val Gly Gly Val Val Ile Ala
            35                  40
```